(12) United States Patent
Fujiyama et al.

(10) Patent No.: US 7,931,865 B2
(45) Date of Patent: Apr. 26, 2011

(54) APPARATUS FOR DETERMINING TOTAL ORGANIC CARBON

(75) Inventors: Yoichi Fujiyama, Kyoto (JP); Hirohisa Abe, Kyoto (JP); Masakazu Akechi, Kyoto (JP); Takeaki Inoue, Kyoto (JP); Takeshi Iharada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 229 days.

(21) Appl. No.: 12/444,563

(22) PCT Filed: Oct. 17, 2006

(86) PCT No.: PCT/JP2006/320625
§ 371 (c)(1),
(2), (4) Date: Apr. 6, 2009

(87) PCT Pub. No.: WO2008/047405
PCT Pub. Date: Apr. 24, 2008

(65) Prior Publication Data
US 2010/0098588 A1    Apr. 22, 2010

(51) Int. Cl.
*G01N 31/12* (2006.01)
*G01N 21/00* (2006.01)
*G01N 31/00* (2006.01)
*G01N 33/00* (2006.01)
*G01N 27/00* (2006.01)
*G01N 15/06* (2006.01)
*G01N 33/48* (2006.01)

(52) U.S. Cl. ........ 422/78; 422/68.1; 422/80; 422/82.01; 422/82.02; 436/145; 436/146

(58) Field of Classification Search .................... None
See application file for complete search history.

(56) References Cited

U.S. PATENT DOCUMENTS
5,132,094 A * 7/1992 Godec et al. ............. 422/68.1
5,171,694 A * 12/1992 Connolly ................. 436/134
6,444,474 B1 * 9/2002 Thomas et al. ........... 436/146
2003/0211626 A1 * 11/2003 Davenport et al. ....... 436/146

FOREIGN PATENT DOCUMENTS
JP    2510368 B2    6/1996
JP    2001-281189 A   10/2001
(Continued)

OTHER PUBLICATIONS
International Search Report for the Application No. PCT/JP2006/320625 mailed Jan. 16, 2007.

*Primary Examiner* — Jill Warden
*Assistant Examiner* — Charles Hammond
(74) *Attorney, Agent, or Firm* — Cheng Law Group, PLLC

(57) ABSTRACT

An apparatus which comprises: an organic-substance oxidation part in which organic substances contained in a sample water supplied are oxidized into carbon dioxide; a carbon dioxide separation part in which the carbon dioxide contained in the sample water is caused to permeate and come into a measurement water; and a conductivity measurement part in which the conductivity of the measurement water is measured. The carbon dioxide separation part comprises: a sample water channel in which sample water flows; an intermediate water part in which intermediate water having a higher pH value in a neutral region than the sample water is present; and a measurement water channel through which the measurement water comprising deionized water flows. The sample water channel is in contact with the intermediate water part through a gas-permeable membrane, and the intermediate water part is in contact with the measurement water channel through a gas-permeable membrane.

16 Claims, 8 Drawing Sheets

FOREIGN PATENT DOCUMENTS

| | | |
|---|---|---|
| JP | 2004-205297 A | 7/2004 |
| JP | 2005-321265 A | 11/2005 |
| JP | 2006-090732 A | 4/2006 |
| WO | WO 91/13362 A1 | 9/1991 |

* cited by examiner

APPARATUS FOR DETERMINING TOTAL ORGANIC CARBON

TECHNICAL FIELD

The present invention relates to an apparatus for determining total organic carbon (TOC) content of sample water (hereinafter, also referred to as a TOC meter). For example, the present invention relates to an apparatus for determining total organic carbon, in which organic substances contained in water having few impurities, called pure water or ultrapure water, are separated from the water by a carbon dioxide separation part to evaluate the TOC content of the water based on a conductivity.

BACKGROUND ART

In order to monitor sample water containing few impurities, such as water for medicine manufacturing, process water for semiconductor manufacturing, cooling water, boiler water, or tap water, TOC of such sample water is determined to quantify the amount of organic substances contained therein.

As a method for determining TOC, a method including the steps of: converting organic substances contained in sample water into carbon dioxide with an oxidation reactor, transferring the carbon dioxide into measurement water through a gas-permeable membrane, and determining the carbon dioxide concentration of the measurement water by measuring the conductivity of the measurement water containing the carbon dioxide transferred from the sample water with a conductivity meter is known (see Patent Documents 1 and 2).

As a method for measuring a conductivity caused by carbon dioxide to determine TOC, a method, in which a difference in the conductivity of sample water before and after oxidation is detected using at least two electrodes provided at positions where the conductivity of the sample water can be measured before and after oxidation, is disclosed (see Patent Document 3). An example of a TOC meter using such a method is A-1000 manufactured by ANATEL.

As a method for accurately determining the TOC content of water containing few impurities, such as water for semiconductor manufacturing or water for medicine manufacturing, with a relatively-compact apparatus, a method, in which organic substances contained in such water are decomposed by UV light into carbon dioxide and the carbon dioxide is separated by a carbon dioxide separation part to measure a conductivity, is known.

Patent Document 1: Japanese Patent No. 2510368
Patent Document 2: Japanese Patent Application Laid-open No. 2006-90732
Patent Document 3: Japanese Patent Application Laid-open No. 2001-281189

DISCLOSURE OF THE INVENTION

Problem(s) to be Solved by the Invention

When organic substances are decomposed by UV light, there is a case where a gas component other than carbon dioxide is generated from a compound containing elements other than carbon, such as a nitrogen compound contained in a sample water, and is then transferred together with carbon dioxide and interferes with conductivity measurement. As a method for avoiding interference caused by such a gas component, a method using, as a gas-permeable membrane, a carbon dioxide selective membrane that allows carbon dioxide to selectively pass through it is proposed. However, a carbon dioxide selective membrane is disadvantageous in that the permeation rate of a gas component is low and therefore, the measurement time becomes long.

It is an object of the present invention to provide a TOC determining apparatus which uses, in its carbon dioxide separation part, a gas-permeable membrane capable of maintaining high-speed measurement and which can reduce the influence of an interfering ingredient.

Means for Solving the Problem

In the present invention, the carbon dioxide separation part uses, as a gas-permeable membrane, a membrane not having carbon dioxide selectivity, such as a porous membrane usually used to maintain high-speed measurement. Further, the carbon dioxide separation part includes an intermediate water part provided between a sample water channel and a measurement water channel and separated from these channels by a gas-permeable membrane. The intermediate water part is provided to allow intermediate water to be retained therein or to flow therethrough. The pH of intermediate water in the intermediate water part is regulated to suppress gasification of an interfering ingredient so that the transfer of the interfering ingredient from the intermediate water part to a conductivity measurement part is suppressed. This makes it possible to achieve both reduction in the influence of the interfering ingredient and high-speed measurement.

More specifically, the present invention is directed to an apparatus for determining total organic carbon including: an organic-substance oxidation part for oxidizing organic substances contained in sample water supplied to carbon dioxide; a carbon dioxide separation part for transferring the carbon dioxide contained in the sample water treated with the organic-substance oxidation part into measurement water; and a conductivity measurement part for measuring the conductivity of the measurement water sent from the carbon dioxide separation part. The carbon dioxide separation part includes a sample water channel through which sample water treated with the organic-substance oxidation part flows, an intermediate water part containing intermediate water having a higher pH value in a neutral region than the sample water flowing through the sample water channel, and a measurement water channel through which measurement water composed of deionized water flows. The sample water channel and the intermediate water part are in contact with each other with a gas-permeable membrane being interposed therebetween, and the intermediate water part and the measurement water channel are in contact with each other with a gas-permeable membrane being interposed therebetween.

In general, in a case where the TOC of sample water is determined by measuring the conductivity of measurement water with a TOC meter having a carbon dioxide separation part, the sample water is made strongly acidic because an acid is added to the sample water for the purpose of removing a dissolved carbon dioxide component, promoting transfer of a gas component into measurement water, and achieving measurement stability. When sample water containing a nitrogen compound such as urea is decomposed by oxidation caused by UV light irradiation under strong acidic conditions, nitric acid and nitrous acid are generated from the nitrogen compound.

As shown in FIG. 4, the ratio between nitrous acid and nitrite ions present in water varies depending on the pH of the water. More specifically, nitrous acid is present as a gas component under acidic conditions, but is present as nitrite ions under neutral to alkaline conditions.

In the case of a conventional TOC determining apparatus having a structure in which sample water and measurement water are in contact with each other with a gas-permeable membrane being interposed therebetween in a carbon dioxide separation part, since the sample water is acidic and the measurement water is neutral, nitrous acid generated in the sample water is transferred through the gas-permeable membrane into the measurement water and is then converted into nitrite ions in the measurement water. Therefore, nitrous acid exerts an influence on conductivity measurement so that the conductivity of the measurement water increases, that is, shifts toward the positive direction.

On the other hand, in the case of the TOC meter according to the present invention, the intermediate water part is provided between the sample water channel and the measurement water channel to contain intermediate water having a higher pH value in a neutral region than sample water flowing through the sample water channel. In this case, nitrous acid generated in the sample water is transferred through a gas-permeable membrane into the intermediate water part, but the ratio of gaseous nitrous acid present in the intermediate water is reduced by keeping the pH of the intermediate water around neutral, and nitrous acid is converted into nitrite ions. Nitrite ions cannot permeate the gas-permeable membrane, and therefore transfer of nitrous acid into measurement water is suppressed.

For example, in a case where deionized water is used as both the intermediate water and the measurement water, the pH of each is kept at 5 to 7 by dissolved carbonic acid. Under such conditions, the carbonic acid component is mostly present as gas, but on the other hand, nitrous acid is mostly present as ions. Since the transfer rate of a gas from the intermediate water to the measurement water is determined by the difference in concentration between them, the transfer rate of nitrous acid mostly present as ions is lower than that of carbonic acid. By appropriately designing the thickness of the gas-permeable membrane interposed between the intermediate water and the measurement water and the area of contact between the membrane and the intermediate water or the measurement water based on the difference between the transfer rate of nitrous acid and the transfer rate of carbonic acid, it is possible to reduce the influence of nitrous acid on a conductivity caused by carbon dioxide.

As described above, according to the present invention, providing the intermediate water part makes it possible to achieve reduction in the influence of an interfering substance while maintaining a high gas permeation rate of carbon dioxide. In the above description, nitrous acid is exemplified as an interfering substance, but the influence of another interfering substance can also be reduced as long as the interfering substance is present as a gas under acidic conditions but is present as an ion under neutral to alkaline conditions.

The intermediate water part allows the intermediate water to stay therein or to flow therethrough. In a case where the intermediate water stays in the intermediate water part, nitrite ions remain in the intermediate water. In this case, there is a problem that remaining nitrite ions affect the next measurement when continuous measurement is carried out. On the other hand, in a case where the intermediate water part is designed as a channel through which the intermediate water flows, no nitrite ions remain in the intermediate water part.

One example of the carbon dioxide separation part is obtained by vertically stacking the sample water channel, the intermediate water part, and the measurement water channel in such a manner that the intermediate water part is interposed between the sample water channel and the measurement water channel to integrate them together.

By vertically stacking the sample water channel, the intermediate water part, and the measurement water channel in such a manner that the intermediate water part is interposed between the sample water channel and the measurement water channel to integrate them together, it is possible to reduce the influence of diffusion of carbon dioxide in intermediate water. This makes it possible to determine TOC even when the amount of the sample water is small, thus resulting in short-time measurement.

In this case, it is preferred that the intermediate water part is designed as a channel through which the intermediate water flows, and is divided by a septum into a sample water-side intermediate water part being in contact with the sample water channel and a measurement water-side intermediate water part being in contact with the measurement water channel, wherein the sample water-side intermediate water part and the measurement water-side intermediate water part are connected to each other through a connecting portion provided at an end of the intermediate water part so that the intermediate water supplied flows from the sample water-side intermediate water part through the connecting portion to the measurement water-side intermediate water part.

For example, in a case where nitrous acid is transferred from the sample water into the intermediate water, some time is required to convert nitrous acid into nitrite ions. If the intermediate water comes into contact with the measurement water with a gas-permeable membrane being interposed therebetween before nitrous acid is converted into nitrite ions, there is a possibility that nitrous acid is transferred into the measurement water. However, by dividing the intermediate water part by the septum into the sample water-side intermediate water part and the measurement water-side intermediate water part, it is possible to convert nitrous acid into nitrite ions during the time when the intermediate water that has come into contact with the sample water is moved until it comes into contact with the measurement water, thereby eliminating the possibility that nitrous acid is transferred into measurement water.

The organic-substance oxidation part and the carbon dioxide separation part may be vertically stacked to integrate them together, and the conductivity measurement part and the carbon dioxide separation part may be vertically stacked to integrate them together. This makes it possible to reduce the whole size of the TOC apparatus.

In the case of another example of the carbon dioxide separation part, the intermediate water part is designed as a channel through which the intermediate water flows, and has a sample water-side intermediate water part being in contact with the sample water channel and a measurement water-side intermediate water part being in contact with the measurement water channel. The sample water-side intermediate water part and the measurement water-side intermediate water part are connected to each other through a connecting channel so that the intermediate water supplied flows from the sample water-side intermediate water part to the measurement water-side intermediate water part. Also in the case of this carbon dioxide separation part, the possibility that nitrous acid is transferred into the measurement water can be eliminated because nitrous acid is converted into nitrite ions during the time when the intermediate water that has come into contact with the sample water is moved until it comes into contact with the measurement water.

In order to improve the reproducibility of measurement results, it is important to keep the ratio between the flow rate of the intermediate water and the flow rate of the measurement water constant. Therefore, the apparatus for determining TOC according to the present invention preferably has a syringe pump having two syringes. In this case, one of the syringes is connected to the intermediate water channel to control the supply of the intermediate water, and the other syringe is connected to the measurement water channel to control the supply of the measurement water. This makes it possible to keep the ratio between the flow rate of the intermediate water and the flow rate of the measurement water constant.

The permeation rate of a gas component through the gas-permeable membrane is proportional to the area of contact between the sample water and the intermediate water or the area of contact between the intermediate water and the measurement water. Therefore, in order to regulate the amount of a gas permeating the gas-permeable membrane, the intermediate water part may have a shielding membrane provided so as to be in contact with at least one of the gas-permeable membranes to cover part of the gas-permeable membrane therewith. By providing such a shielding membrane, it is possible to regulate the area of the gas-permeable membrane so that the permeation rate of a gas component is regulated.

One example of the organic-substance oxidation part includes a channel, through which the sample water flows, and a UV light incident portion for irradiating the sample water flowing through the channel with UV light. Such an organic-substance oxidation part for oxidizing organic substances by UV irradiation does not need a heat-applying portion or a pressure-applying portion, and therefore can be made compact and is easily integrated with another structural component. In order to lengthen the UV light exposure time to enhance the oxidation efficiency of the organic-substance oxidation part, the channel through which the sample water flows may meander in the UV light incident portion to increase a channel length.

In order to lengthen the time during which the sample water and the intermediate water are in contact with each other in the carbon dioxide separation part to enhance the efficiency of gas transfer from the sample water to the intermediate water, part of the sample water channel of the carbon dioxide separation part being in contact with the gas-permeable membrane may meander to increase a channel length.

In order to lengthen the time during which the intermediate water and the measurement water are in contact with each other in the carbon dioxide separation part to enhance the efficiency of gas transfer from the intermediate water to the measurement water, part of the measurement water channel of the carbon dioxide separation part being in contact with the gas-permeable membrane may meander to increase a channel length.

In a case where the intermediate water part of the carbon dioxide separation part is designed as a channel through which the intermediate water flows, part of the intermediate water part being in contact with the gas-permeable membrane may meander to increase a channel length to lengthen the retention time of the intermediate water in the intermediate water part.

It is important that the pH of intermediate water is appropriately set. The intermediate water may be pure water or deionized water or may be a buffer solution having a pH within a neutral region.

Effects of the Invention

In the TOC meter according to the present invention, the carbon dioxide separation part includes the intermediate water part that allows intermediate water, which has a higher pH value in a neutral region than sample water flowing through the sample water channel of the carbon dioxide separation part, to stay therein or to flow therethrough, and the sample water channel and the intermediate water part are in contact with each other with a gas-permeable membrane being interposed therebetween, and the intermediate water part and the measurement water channel are in contact with each other with a gas-permeable membrane being interposed therebetween. It follows that an interfering ingredient is trapped in the intermediate water to suppress the transfer of the interfering ingredient from the intermediate water to measurement water. Therefore, it is possible to carry out rapid continuous measurement with stability while the influence of the interfering ingredient is reduced.

Figure 1:
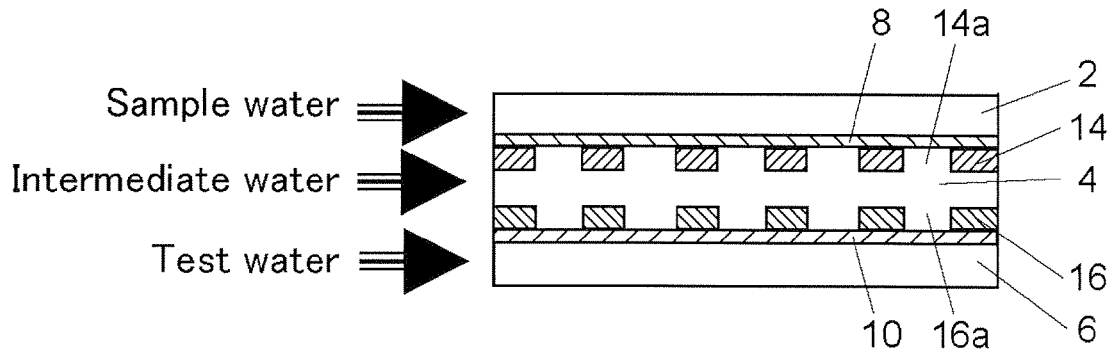
FIG. 1 is a schematic sectional view of one example of a carbon dioxide separation part for use in a TOC meter according to the present invention.

DESCRIPTION OF THE REFERENCE NUMERALS 2 sample water channel
4 intermediate water part
4a sample water-side intermediate water part
4b measurement water-side intermediate water part
4c connecting portion
4d connecting channel
6 measurement water channel
8, 10 gas-permeable membrane
14, 16 shielding membrane
18 septum
20, 40 carbon dioxide separation part
24 organic-substance oxidation part
26 UV lamp
30 ion-exchange resin
34 conductivity meter
42, 44 syringe
46 syringe pump

BEST MODES FOR CARRYING OUT THE INVENTION

Figure 2:
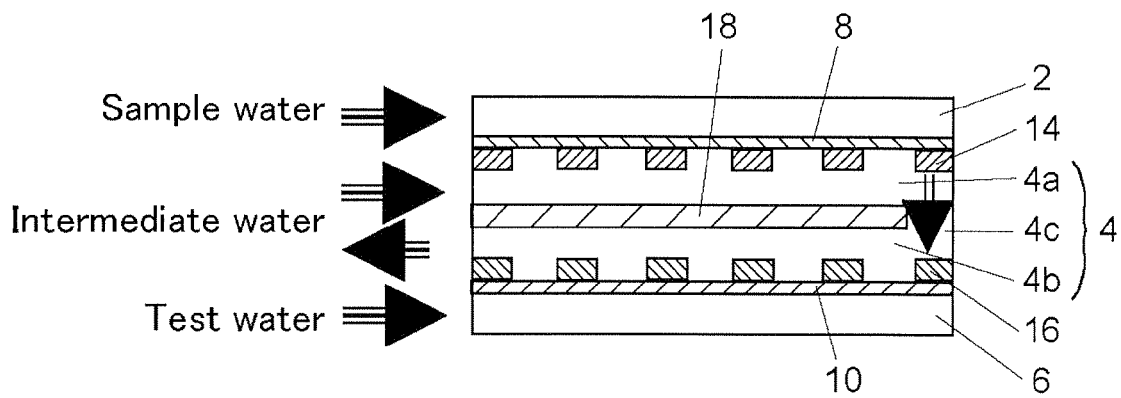
FIG. 2 is a schematic sectional view of another example of the carbon dioxide separation part.
Figure 3:
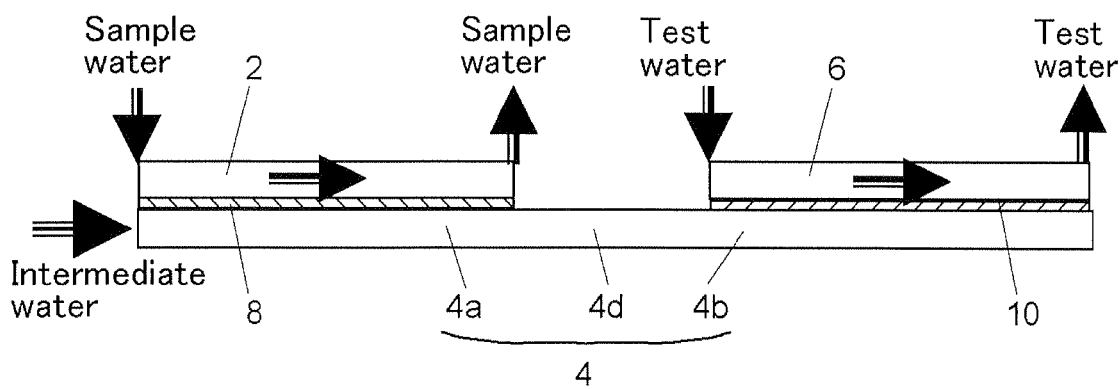
FIG. 3 is a schematic sectional view of still another example of the carbon dioxide separation part.
Figure 4:
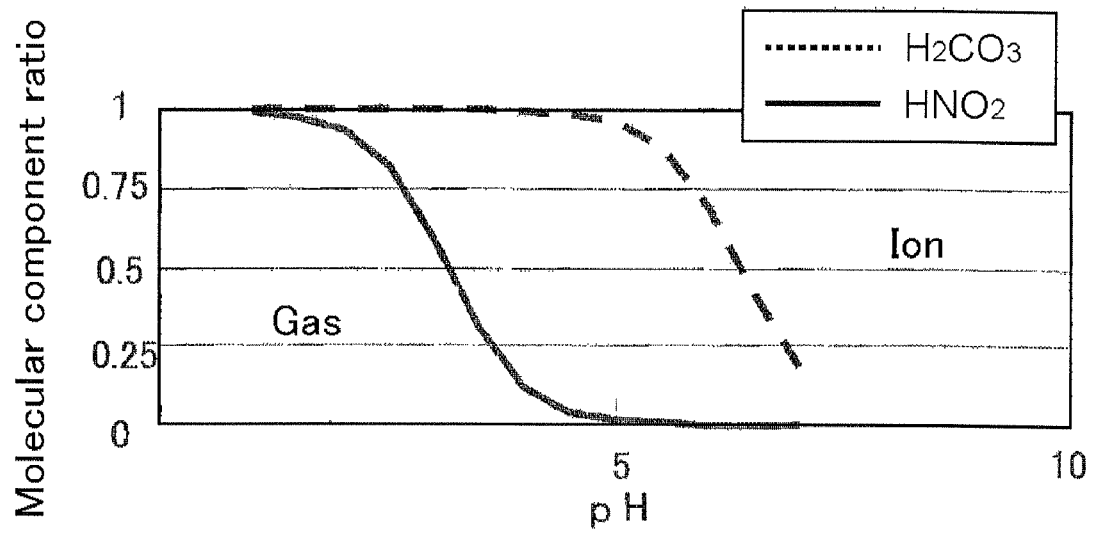
FIG. 4 is a graph showing the relationship between the ratio of molecular nitrous acid or molecular carbon dioxide and pH.

FIGS. 1 to 3 are schematic sectional views of some examples of a carbon dioxide separation part according to the present invention. In the following description, there are some values indicating specific dimensions, but these values are merely examples and are not intended to limit the scope of the present invention.

The carbon dioxide separation part shown in FIG. 1 is obtained by vertically stacking a sample water channel 2, an intermediate water part 4, and a measurement water channel 6 in such a manner that the intermediate water part 4 is interposed between the sample water channel 2 and the measurement water channel 6 to integrate them together. The sample water channel 2 is provided to allow sample water, which has been treated with an organic-substance oxidation part (not shown) for oxidizing organic substances contained in sample water supplied to carbon dioxide, to flow therethrough. The intermediate water part 4 is provided to allow intermediate water having a higher pH value in a neutral region than the sample water to flow therethrough or to stay therein. The intermediate water part 4 is preferably designed as a channel through which the intermediate water flows. The measurement water channel 6 is provided to allow measurement water composed of deionized water to flow therethrough. The sample water channel 2 and the intermediate water part 4 are in contact with each other with a gas-permeable membrane 8 being interposed therebetween. The intermediate water part 4 and the measurement water channel 6 are in contact with each other with a gas-permeable membrane 10 being interposed therebetween.

An example of a method for reducing the transfer rate of an interfering ingredient such as nitrous acid is optimization of the area of the gas-permeable membrane. Therefore, in the case of this carbon dioxide separation part, in order to regulate the area of contact between the sample water and the intermediate water, a shielding membrane 14 having openings 14a is provided in the intermediate water part 4 on the sample water channel 2 side thereof. In addition, in order to regulate the area of contact between the intermediate water and the measurement water, a shielding membrane 16 having openings 16a is also provided in the intermediate water part 4 on the measurement water channel 6 side thereof. The shielding membranes 14 and 16 are not particularly limited, and examples thereof include a film of an adhesive fluororesin (e.g., NEOFLON EFEP (which is a trademark of DAIKIN INDUSTRIES, Ltd.)) or a film of PDMS (polydimethylsiloxane) (e.g., SYLGARD 184 (which is a trademark of Dow Corning)), each having a thickness of about 100 µm.

The carbon dioxide separation part shown in FIG. 2 has the intermediate water part 4 designed as a channel through which the intermediate water flows. The intermediate water part 4 is separated by a septum 18 into a sample water-side intermediate water part 4a being in contact with the sample water channel 2 and a measurement water-side intermediate water part 4b being in contact with the measurement water channel 6. The sample water-side intermediate water part 4a and the measurement water-side intermediate water part 4b are connected to each other through a connecting portion 4c provided at an end of the intermediate water part 4. The intermediate water is supplied so as to flow from the sample water-side intermediate water part 4a through the connecting portion 4c to the measurement water-side intermediate water part 4b. The other structural components of the carbon dioxide separation part shown in FIG. 2 are the same as those of the carbon dioxide separation part shown in FIG. 1.

The carbon dioxide separation part shown in FIG. 3 has the intermediate water part 4 designed as a channel through which the intermediate water flows. The intermediate water part 4 has a structure in which the sample water-side intermediate water part 4a being in contact with the sample water channel 2 and the measurement water-side intermediate water part 4b being in contact with the measurement water channel 6 are separated from each other. The sample water-side intermediate water part 4a and the measurement water-side intermediate water part 4b are connected to each other through a connecting channel 4d. The intermediate water is supplied so as to flow from the sample water-side intermediate water part 4a to the measurement water-side intermediate water part 4b. The sample water channel 2 and the intermediate water part 4 are in contact with each other with the gas-permeable membrane 8 being interposed therebetween. The intermediate water part 4 and the measurement water channel 6 are in contact with each other with the gas-permeable membrane 10 being interposed therebetween.

The measurement water discharged from each of the carbon dioxide separation parts shown in FIGS. 1 to 3 is introduced into a conductivity measurement part (not shown) to measure the conductivity thereof.

Figure 5:
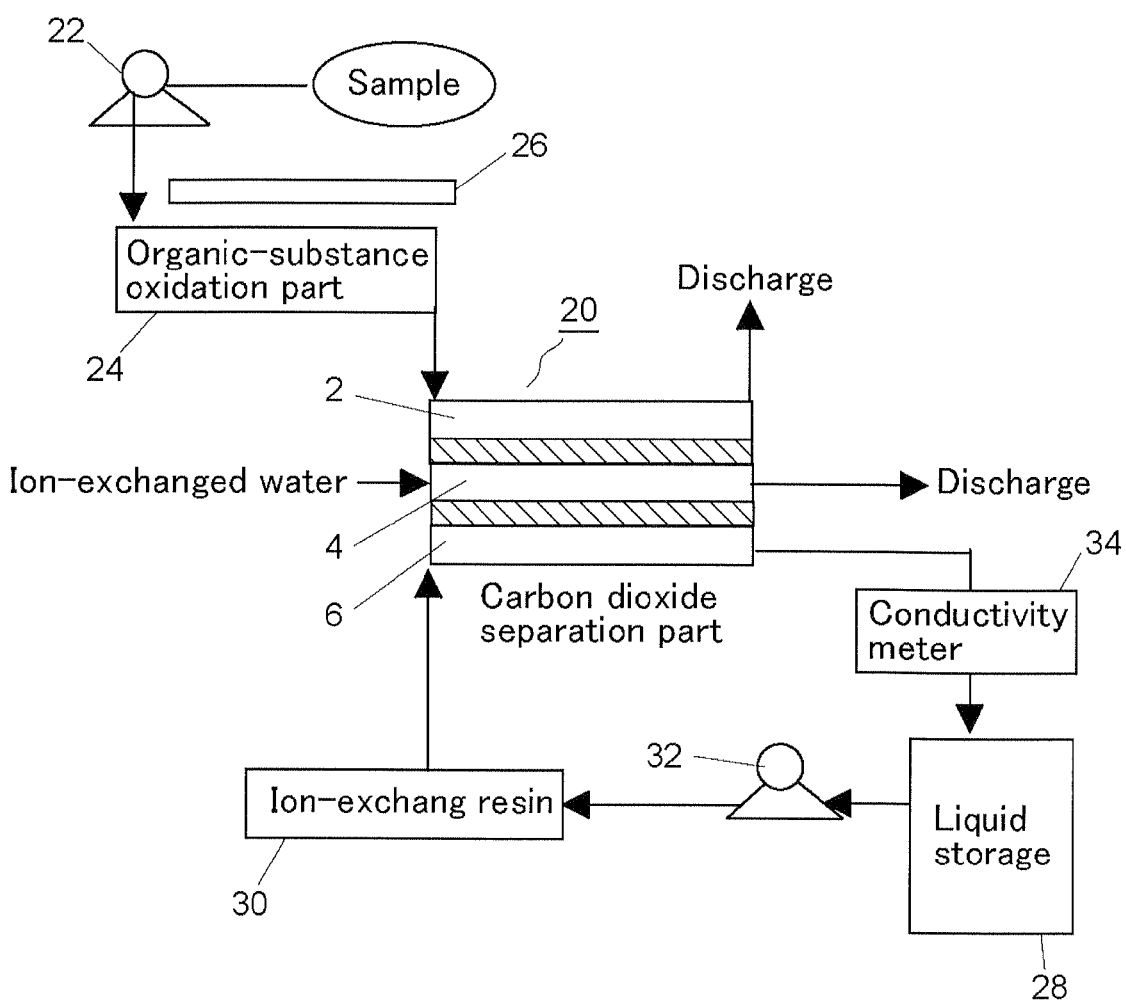
FIG. 5 is a schematic view of a TOC meter according to a first embodiment of the present invention.

FIG. 5 is a schematic view of a TOC meter according to a first embodiment of the present invention. Sample water is supplied by a pump 22 to the sample water channel of the carbon dioxide separation part 20 shown in FIG. 1 or 2 through an organic-substance oxidation part 24. The organic-substance oxidation part 24 has a UV irradiation portion for irradiating the sample water with UV light emitted from a UV lamp 26. When the sample water flows through the UV irradiation portion, organic substances contained in the sample water are oxidized by UV irradiation to carbon dioxide. The organic-substance oxidation part 24 may be integrated with or separated from the carbon dioxide separation part 20. In the latter case, the organic-substance oxidation part 24 and the carbon dioxide separation part 20 are connected to each other through a channel. After passing through the sample water channel 2 of the carbon dioxide separation part 20, the sample water is discharged.

Ion-exchanged water as deionized water is supplied to the measurement water channel 6 of the carbon dioxide separation part 20. More specifically, the ion-exchanged water is supplied in such a manner that pure water stored in a liquid storage 28 is sucked by a pump 32 and sent through an ion-exchange resin 30 to the measurement water channel 6 of the carbon dioxide separation part 20. After the measurement water passes through the measurement water channel 6, the conductivity of the measurement water is measured by a conductivity meter 34. The conductivity of the measurement water is a conductivity caused by carbon dioxide transferred from the intermediate water into the measurement water in the carbon dioxide separation part 20. After passing through the conductivity meter 34, the measurement water is returned to the liquid storage 28 and is then reused. The conductivity meter 34 may be integrated with or separated from the carbon dioxide separation part 20. In the latter case, the conductivity meter 34 and the carbon dioxide separation part 20 are connected to each other through a channel.

Pure water or deionized water is supplied as the intermediate water to the intermediate water channel 4. Alternatively, the deionized water treated with the ion-exchange resin 30 may also be supplied as the intermediate water to the intermediate water channel 4. The intermediate water is in contact with the sample water with the sample water channel-side gas-permeable membrane being interposed therebetween, and is also in contact with the measurement water with the measurement water channel-side gas-permeable membrane being interposed therebetween. After passing through the intermediate water channel 4, the intermediate water is discharged.

Figure 6:
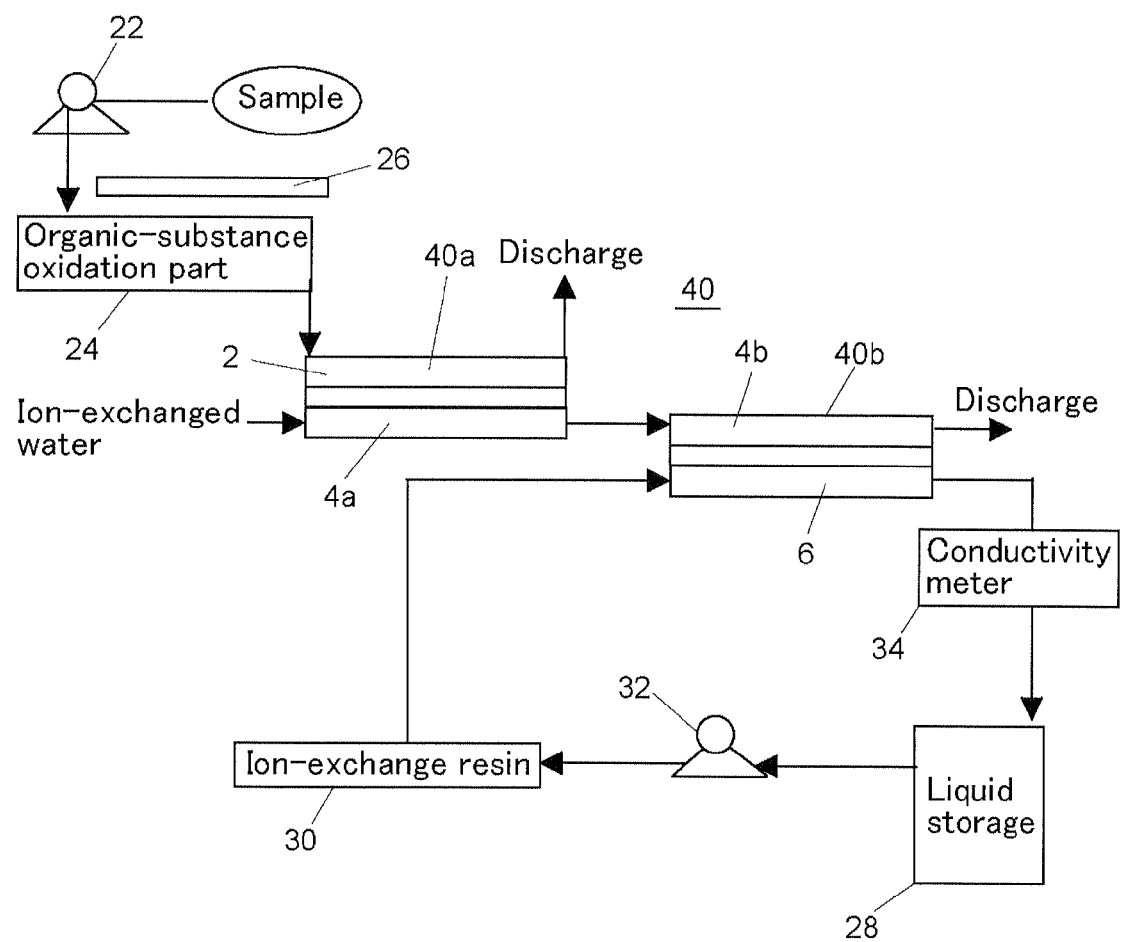
FIG. 6 is a schematic view of a TOC meter according to a second embodiment of the present invention.

FIG. 6 is a schematic view showing the structure of a TOC meter according to another embodiment of the present invention which uses the carbon dioxide separation part shown in FIG. 3. A carbon dioxide separation part 40 is separated into a sample water-side gas exchange part 40a and a measurement water-side gas exchange part 40b. The intermediate water channel is separated into a sample water-side intermediate water channel 4a and a measurement water-side intermediate water channel 4b, and these intermediate water channels 4a and 4b are connected to each other through a connecting channel. The other structural components of the TOC meter shown in FIG. 6 are the same as those of the TOC meter shown in FIG. 5.

Figure 7:
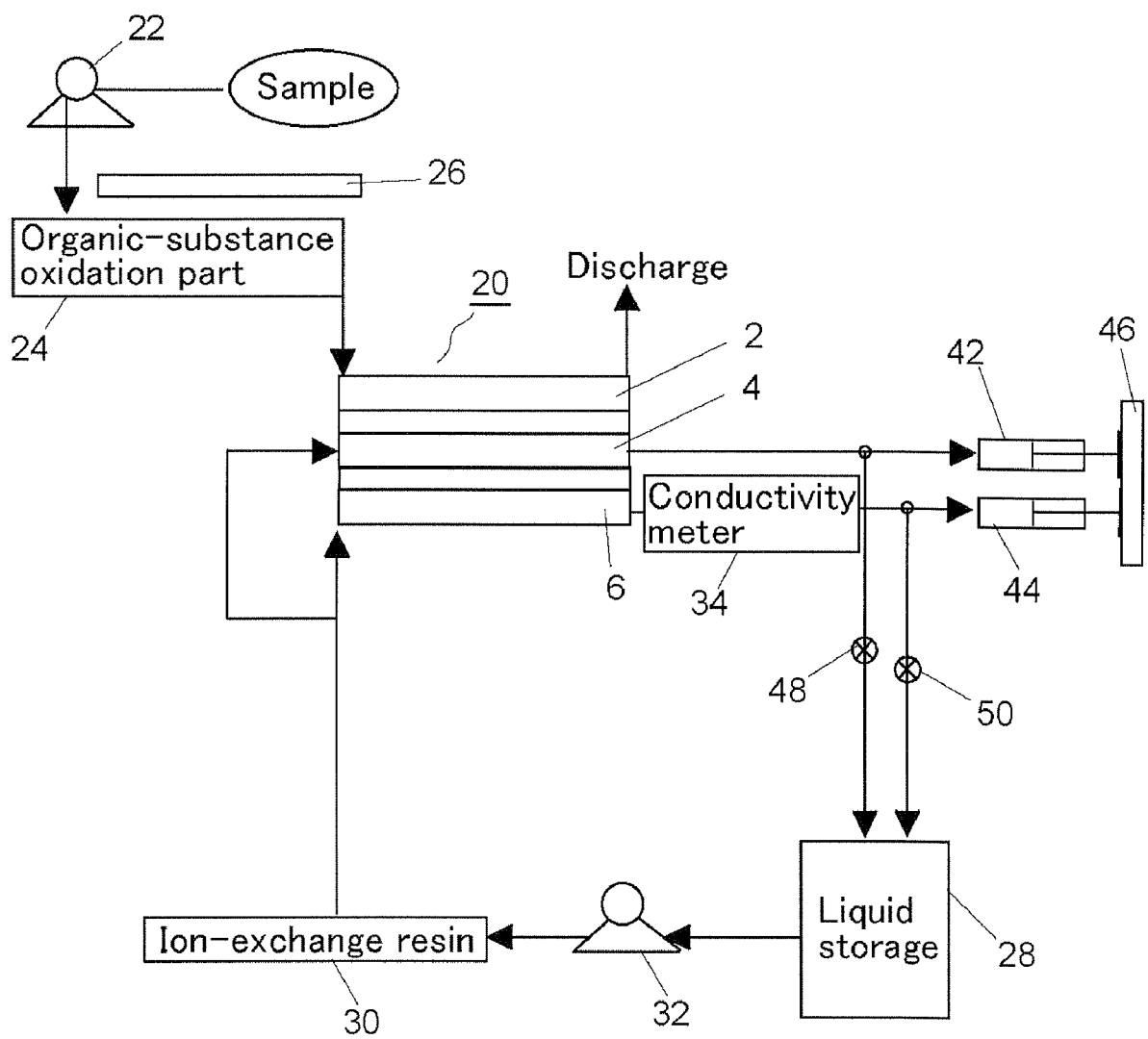
FIG. 7 is a schematic view of a TOC meter according to a third embodiment of the present invention.

FIG. 7 shows another example of a TOC meter which uses a shared syringe pump to keep the ratio between the flow rate of the intermediate water and the flow rate of the measurement water constant. As in the case of the TOC meter shown in FIG. 5, the TOC meter shown in FIG. 7 uses the carbon dioxide separation part 20 shown in FIG. 1 or 2, but may use the carbon dioxide separation part as shown in FIG. 3 in which the sample water-side gas exchange part and the measurement water-side gas exchange part are separated from each other. As the intermediate water and the measurement water, the ion-exchanged water treated with the ion-exchange resin 30 is supplied by the pump 32. The measurement water flows through the measurement water channel 6 into the conductivity meter 34. The intermediate water flows through the intermediate water channel 4. A channel for returning the intermediate water to the liquid storage 28 has a valve 48, and a channel for returning the measurement water to the liquid storage 28 has a valve 50. One syringe pump 46 has two syringes 42 and 44, and these syringes 42 and 44 are connected to the channel having the valve 48 and the channel having the valve 50, respectively, to regulate the flow rates of the intermediate water and the measurement water. In a case where the intermediate water and the measurement water are allowed to flow through their respective channels, the intermediate water and the measurement water are sucked into the syringes 42 and 44 at the same time in a state where the valves 48 and 50 are closed. This makes it possible to allow the intermediate water and the measurement water to flow at a flow rate determined by the inner diameter of the syringe 42 and 44 respectively. After the completion of measurement, the valves 48 and 50 are opened, and the syringes 42 and 44 are operated to discharge the intermediate water and the measurement water contained therein to return the intermediate water and the measurement water to the liquid storage 28.

As described above, in a case where the intermediate water discharged from the intermediate water channel 4 and the measurement water discharged from the measurement water channel 6 are sucked into the two syringes 42 and 44 connected to the one syringe pump 46 at the same time, the ratio between the flow rate of the intermediate water and the flow rate of the measurement water can be kept at a predetermined constant value by appropriately selecting the diameters of the syringes 42 and 44. By keeping the ratio between the flow rate of the intermediate water and the flow rate of the measurement water constant, it is possible to keep the distribution ratio of a gas component between the intermediate water and the measurement water constant, thereby enhancing measurement reproducibility.

Hereinbelow, an integrated TOC meter according to the present invention, in which the organic-substance oxidation part 24, the carbon dioxide separation part 20, and the conductivity meter 34 are integrated together, will be described with reference to FIG. 8. It is to be noted that in a case where distinction should be made between the front surface and the back surface of each substrate, the upper surface and the lower surface thereof shown in FIG. 8 will be referred to as the "front surface" and the "back surface", respectively.

The organic-substance oxidation part 24 is constituted from a substrate 60 through which UV light enters and a substrate 62 bonded to the substrate 60. As the substrate 60, a quartz substrate that allows UV light to pass through it is used to decompose organic substances by UV light. The substrate 60 has a UV light incident portion through which UV light enters, a through hole 64 provided as a sample water inlet, and a through hole 66 provided as a sample water outlet. Also, as the substrate 62, a quartz substrate is used. In the front surface of the substrate 62, an oxidation channel 68 whose one end is located at a position corresponding to the sample water inlet 64 is provided. In the back surface of the substrate 62, the sample water channel 2 whose one end is located at a position corresponding to the sample water outlet 66 is provided. Further, the substrate 62 has a through hole 70 that connects the other end of the oxidation channel 68 and the other end of the sample water channel 2 together, and a through hole 72 that connects the one end of the sample water channel 2 and the sample water outlet 66 together. On the back surface of the substrate 62, that is, on the surface of the substrate 62 opposite to the surface being in contact with the substrate 60, a UV-shielding metal film 33 that defines a UV-irradiated region is provided. As such a UV-shielding metal film 33, for example, a Pt/Ti film (i.e., a film obtained by forming a platinum film on a titanium film serving as an adhesive layer) having a thickness of 0.05 μm or more is used.

The oxidation channel 68 and the sample water channel 2 are not particularly limited in their size, and may have, for example, a width of about 1 mm, a depth of about 0.2 mm, and a length of about 200 mm. The oxidation channel 68 and the sample water channel 2 can be formed by processing such as wet etching or dry etching. The through holes 64, 66, and 70 can be formed by sandblasting or the like. The substrates 60 and 62 can be bonded together by hydrofluoric acid bonding.

The conductivity meter 34 is formed by bonding together a Pt/Ti film electrode pattern 76 provided on a quartz substrate 74 and the back surface of a quartz substrate 80 with a film 78, from which a channel portion has been cut out, being interposed therebetween.

Examples of the film 78 include a film of an adhesive fluororesin (e.g., NEOFLON EFEP (which is a trademark of DAIKIN INDUSTRIES, Ltd.)) or a film of PDMS (polydimethylsiloxane) (e.g., SYLGARD 184 (which is a trademark of Dow Corning)), each having a thickness of 100 μm. On the electrode pattern 76, a channel, through which the measurement water flows, is formed by the film 78.

The electrode pattern 76 can be obtained by forming a Pt/Ti film by sputtering and patterning the Pt/Ti film by photolithography and etching usually used in the fields of semiconductor manufacture and microfabrication, but a method for forming the electrode pattern 76 is not particularly limited. The film for forming a channel on the electrode pattern 76 is not limited to a NEOFLON film or a PDMS film. A method for forming a channel on the electrode pattern 76 is not limited to a method using a NEOFLON film and a method using a PDMS film. For example, the channel on the electrode pattern 76 can be formed by using an adhesive organic film or an adhesive-coated thin film.

In the front surface of the quartz substrate 80, the measurement water channel 6 is provided. The quartz substrate 80 has a measurement water branch channel 82 connected to one end of the measurement water channel 6 and a through hole 84 that connects the other end of the measurement water channel 6 to the channel provided on the electrode pattern 76 of the conductivity meter 34. In addition, the quartz substrate 80 also has a through hole 86 provided as an intermediate water branch channel, through which intermediate water is introduced into the intermediate water channel, and a through hole 88 provided as an intermediate water outlet through which the intermediate water is discharged. The thickness of the quartz substrate 80 is not particularly limited, and may be, for example, 1 mm.

The quartz substrate 74 also has a through hole 90 provided as an ion-exchanged water inlet for supplying ion-exchanged water as deionized water and a through hole 92 provided as an ion-exchanged water outlet for discharging excess ion-exchanged water. The channel formed by the PDMS film 78 interposed between the substrates 74 and 80 connects the ion-exchanged water inlet 90 to the measurement water branch channel 82, the intermediate water branch channel 86, and the ion-exchanged water outlet 92.

In addition, the quartz substrate 74 also has a through hole 94 provided as a measurement water outlet for discharging measurement water, which has been subjected to measurement, from the channel formed on the electrode pattern 76 of the conductivity meter 34 and a through hole 96 provided as an intermediate water outlet for discharging intermediate water. The through hole 96 is connected with the through hole 88 provided in the quartz substrate 80 to discharge the intermediate water.

The back surface of the substrate 62 constituting the organic-substance oxidation part 24 and the front surface of the substrate 80 constituting a unit as the conductivity meter 34 are bonded together with the two gas-permeable membranes 8 and 10, which constitute the carbon dioxide separation part, being interposed therebetween. Between the gas-permeable membranes 8 and 10, a PDMS film 98 is interposed to create a gap corresponding to the thickness of the PDMS film 98. The intermediate water channel 4 is formed by patterning the PDMS film 98. The intermediate water channel 4 has one end connected to the intermediate water branch channel 86 provided in the quartz substrate 80 to introduce the intermediate water to the intermediate water channel 4, and the other end connected to the through hole 88 provided to discharge the intermediate water.

The interface between the gas-permeable membrane 8 and the substrate 62 is sealed with a film such as a PDMS film to form the sample water channel 2 between the gas-permeable membrane 8 and the substrate 62. Also, the interface between the gas-permeable membrane 10 and the substrate 80 is sealed with a film such as a PDMS film to form the measurement water channel 6 between the gas-permeable membrane 10 and the substrate 80.

The gas-permeable membranes 8 and 10 are not particularly limited as long as they have no carbon dioxide selectivity. An example of a gas-permeable membrane to be used as such gas-permeable membranes 8 and 10 is a porous fluororesin membrane (e.g., a 30 μm-thick POREFLON membrane manufactured by Sumitomo Electric Industries, Ltd.).

In the case of this TOC meter, the sample water is introduced through the sample water inlet 64 provided in the substrate 60, and flows through the oxidation channel 68 and the sample water channel 2, and is then discharged through the sample water outlet 66. By the time the sample water introduced through the sample water inlet 64 is discharged through the sample water outlet 66, the sample water is oxidized by UV irradiation in the oxidation part 24, and is then brought into contact with the intermediate water with the gas-permeable membrane 8 of the carbon dioxide separation part 20 being interposed between the sample water and the intermediate water so that a gas component such as carbon dioxide is distributed to the intermediate water.

The ion-exchanged water is generated outside the TOC meter, and is introduced through the ion-exchanged water inlet 90. Most of the ion-exchanged water introduced into the TOC meter is directly discharged through the ion-exchanged water outlet 92, and only the needed amount of the ion-exchanged water is supplied to the measurement water channel 6 through the measurement water branch channel 82 and to the intermediate water channel 4 through the intermediate water branch channel 86.

The intermediate water channel 4 is in contact with both the gas-permeable membrane 8 being in contact with sample water and the gas-permeable membrane 10 being in contact with measurement water. Therefore, a gas component transferred from the sample water comes to equilibrium with ions in the intermediate water and is distributed to the measurement water. Then, the intermediate water is discharged outside through the intermediate water outlets 88 and 96. While flowing through the measurement water channel 6, the measurement water receives the gas component, and then flows through the conductivity meter 34 and is discharged through the measurement water outlet 94.

Figure 8:
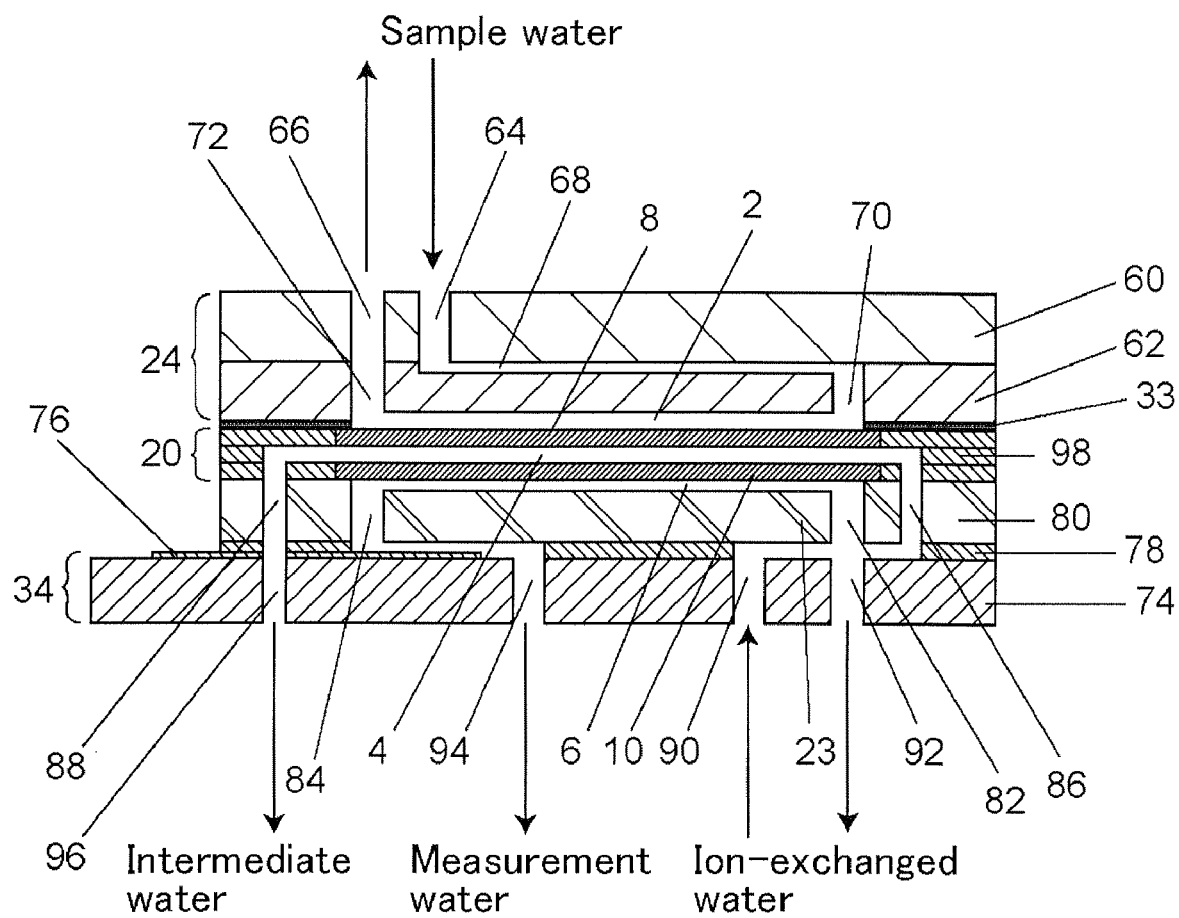
FIG. 8 is a sectional view of an integrated TOC meter according to the present invention.
Figure 9:
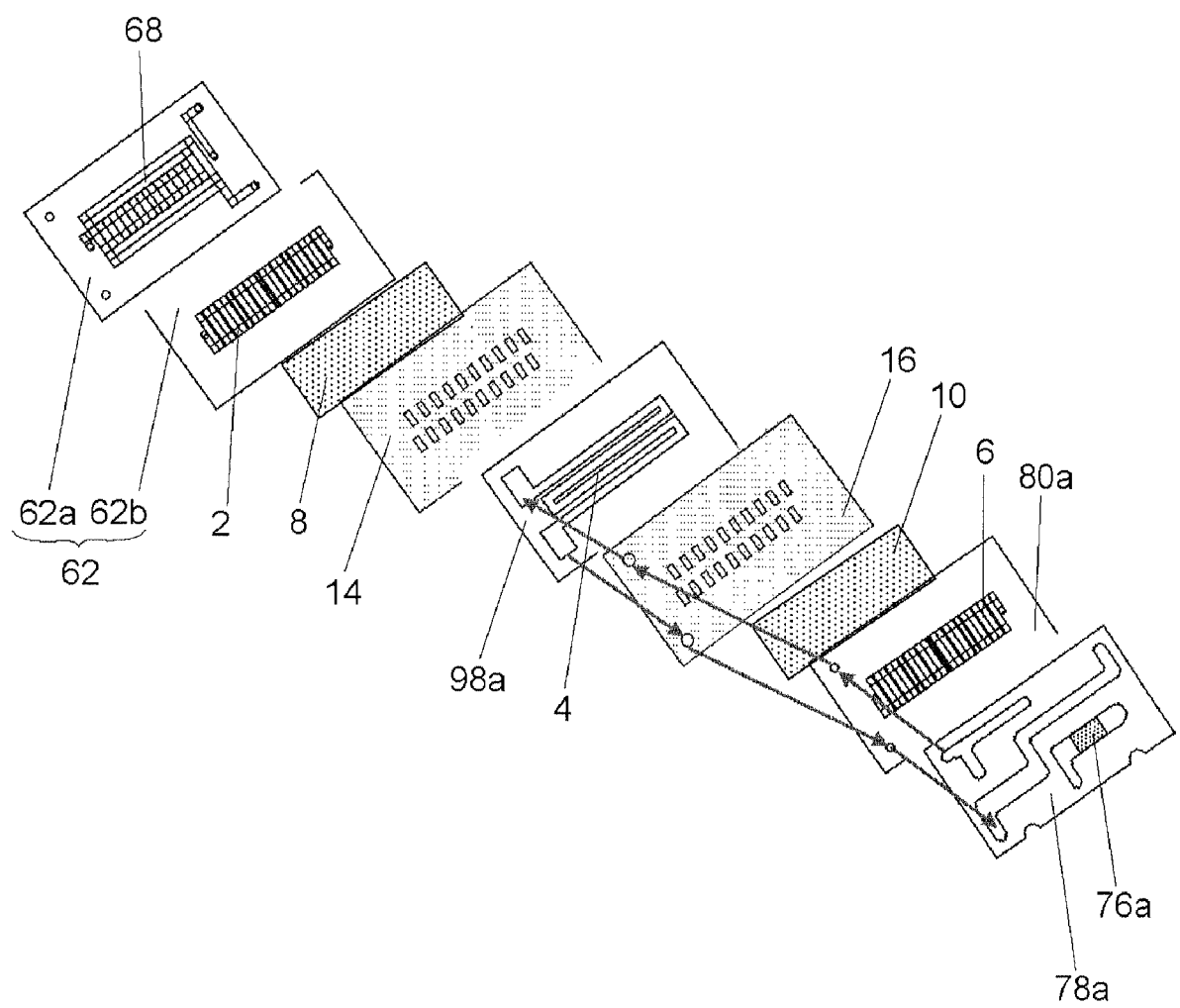
FIG. 9 is an exploded perspective view of another integrated TOC meter according to the present invention.

FIG. 9 is an exploded perspective view of another embodiment of the integrated TOC meter according to the present invention as shown in FIG. 8. The oxidation channel 68 is formed as a groove having a depth of 0.6 mm on a front surface 62a of the quartz substrate 62, and the sample water channel 2 is formed as a groove having a thickness of 60 μm on a back surface 62b of the quartz substrate 62. The intermediate water channel 4 is formed as a through groove in an adhesive fluororesin (e.g., NEOFLON EFEP (which is a trademark of DAIKIN INDUSTRIES, Ltd.)) membrane 98a having a thickness of 100 μm, and the measurement water channel 6 is formed as a groove having a depth of 60 μm on a surface 80a of the quartz substrate 80 (see FIG. 8) opposed to the gas-permeable membrane 10. The oxidation channel 68, the sample water channel 2, the intermediate water channel 4, and the measurement water channel 6 are formed in a meandering shape to increase their channel length. These channels 2, 6, and 68 can be formed by, for example, sandblasting.

The electrode pattern of the conductivity meter 34 is formed at a position shown by the reference numeral 76a in FIG. 9 on the surface of the substrate 80 opposite to the surface 80a, and the surface of the quartz substrate 74 (see FIG. 8) facing the substrate 80. A channel through which the measurement water flows is formed by cutting the pattern of the channel out of a 100 μm-thick adhesive fluororesin (e.g., NEOFLON EFEP (which is a trademark of DAIKIN INDUSTRIES, Ltd.)) membrane 78a. The membrane 78a is interposed between the substrate 80 and the substrate 74.

In order to regulate the area of contact between the sample water and the intermediate water, the shielding membrane 14 having openings is provided between the intermediate water channel 4 and the sample water channel 2. In addition, in order to regulate the area of contact between the intermediate water and the measurement water, the shielding membrane 16 having openings is provided also between the intermediate water channel 4 and the measurement water channel 6. Each of the shielding membranes 14 and 16 is, for example, a membrane of an adhesive fluororesin (e.g., NEOFLON EFEP (which is a trademark of DAIKIN INDUSTRIES, Ltd.)) having a thickness of 25 μm. Each of the gas-permeable membranes 8 and 10 is, for example, a 30 μm-thick fluororesin porous material (e.g., POREFLON (which is a trademark of DAIKIN INDUSTRIES, Ltd.)).

The TOC meter shown in FIG. 9 is formed in the following manner. The above-described quartz substrate 62, gas-permeable membrane 8, shielding membrane 14, adhesive fluorororesin membrane 98a, shielding membrane 16, gas-permeable membrane 10, quartz substrate 80, electrode pattern 76a, and adhesive fluororesin membrane 78a are stacked in this order from top to bottom. A substrate corresponding to the quartz substrate 60 shown in FIG. 8 is provided as an uppermost layer and a substrate corresponding to the quartz substrate 74 shown in FIG. 8 is provided as a lowermost layer. All of them are bonded and integrated together.

Figure 10:
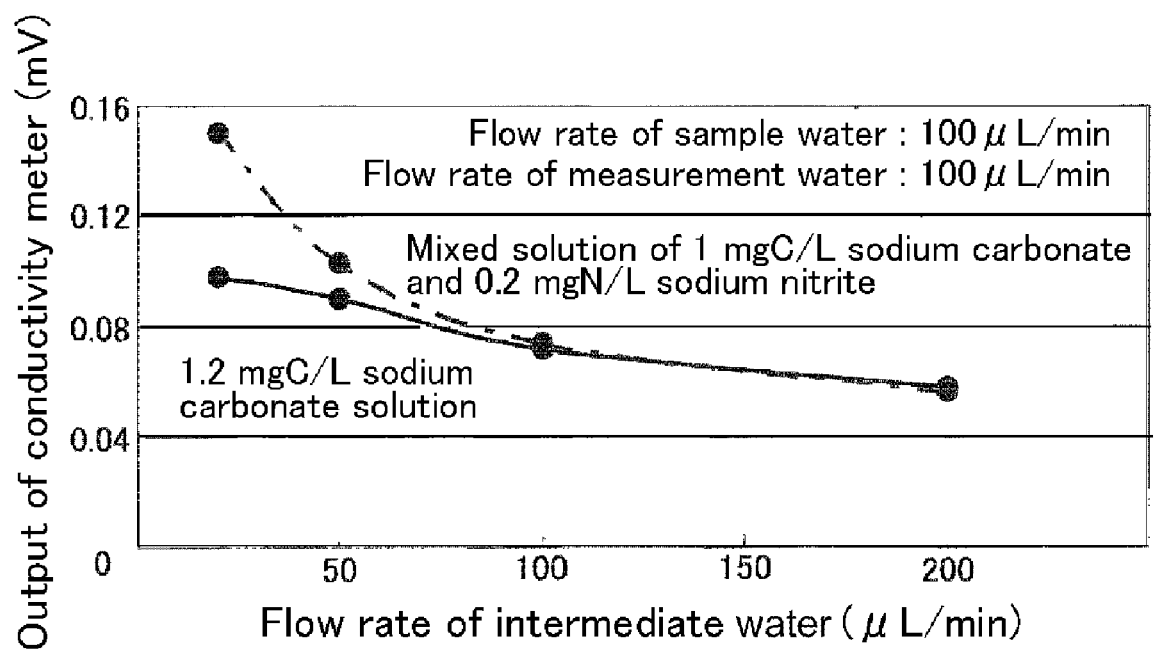
FIG. 10 is a graph showing the relationship between the influence of an interfering ingredient and the flow rate of intermediate water.

In the present invention, the influence of nitrous acid as an interfering ingredient varies depending on the length of time during which nitrous acid is transferred from intermediate water to measurement water. FIG. 10 shows the results of a test for evaluating a change in the influence of nitrous acid when sample water and measurement water were allowed to flow at a flow rate of 100 µL/min while the flow rate of intermediate water was changed. In FIG. 10, a broken line indicates a result obtained when an aqueous sodium carbonate solution was used as sample water, and a solid line indicates a result obtained when an aqueous sodium carbonate solution containing sodium nitrite as an interfering ingredient was used as sample water. Both the solutions used as sample water had the same total solute concentration.

As can be seen from the results, when the flow rate of the intermediate water was low, part of nitrous acid was distributed to the measurement water and therefore the influence of interference caused by nitrous acid appeared because the retention time of nitrous acid in the intermediate water channel was long, but the influence of interference caused by nitrous acid was gradually reduced as the flow rate of the intermediate water was increased.

The above-described embodiments are merely examples, and are not intended to limit the use of substrate materials, sealing materials, and the like having the same functions as described above. Further, it is not absolutely necessary to integrate together the organic-substance oxidation part, the carbon dioxide separation part, and the conductivity meter into a chip. The device structure of the TOC meter according to the present invention is not limited to a vertically-stacked structure as shown in FIG. 8 or 9, and the same function can be obtained also by a horizontally-extended structure.

What is claimed is:

1. An apparatus for determining total organic carbon, comprising:
   an organic-substance oxidation part for oxidizing organic substances contained in sample water supplied to carbon dioxide;
   a carbon dioxide separation part having a sample water channel through which the sample water treated with the organic-substance oxidation part flows, an intermediate water part containing intermediate water having a higher pH value in a neutral region than the sample water flowing through the sample water channel, and a measurement water channel through which measurement water composed of deionized water flows, the sample water channel and the intermediate water part being in contact with each other with a gas-permeable membrane being interposed therebetween and the intermediate water part and the measurement water channel being in contact with each other with a gas-permeable membrane being interposed therebetween; and
   a conductivity measurement part for measuring a conductivity of the measurement water sent from the carbon dioxide separation part.

2. The apparatus for determining total organic carbon according to claim 1, wherein the intermediate water part is formed as a channel.

3. The apparatus for determining total organic carbon according to claim 1, wherein the carbon dioxide separation part is formed by vertically stacking the sample water channel, the intermediate water part, and the measurement water channel with the intermediate water part being interposed between the sample water channel and the measurement water channel to integrate them together.

4. The apparatus for determining total organic carbon according to claim 3,
   wherein the channel constituting the intermediate water part is divided by a septum into a sample water-side intermediate water part being in contact with the sample water channel and a measurement water-side intermediate water part being in contact with the measurement water channel, the sample water-side intermediate water part and the measurement water-side intermediate water part being connected to each other through a connecting portion provided at an end of the intermediate water part, and
   wherein the intermediate water is supplied so as to flow from the sample water-side intermediate water part through the connecting portion to the measurement water-side intermediate water part.

5. The apparatus for determining total organic carbon according to claim 3, wherein the organic-substance oxidation part and the carbon dioxide separation part are vertically stacked to integrate them together.

6. The apparatus for determining total organic carbon according to claim 3, wherein the conductivity measurement part and the carbon dioxide separation part are vertically stacked to integrate them together.

7. The apparatus for determining total organic carbon according to claim 2,
   wherein the channel constituting the intermediate water part has a sample water-side intermediate water part being in contact with the sample water channel and a measurement water-side intermediate water part being in contact with the measurement water channel, the sample water-side intermediate water part and the measurement water-side intermediate water part being connected to each other through a connecting channel, and
   wherein the intermediate water is supplied so as to flow from the sample water-side intermediate water part to the measurement water-side intermediate water part.

8. The apparatus for determining total organic carbon according to claim 2, further comprising a syringe pump having two syringes, wherein one of the syringes is connected to the intermediate water channel to control the supply of the intermediate water and the other syringe is connected to the measurement water channel to control the supply of the measurement water so that the flow rate ratio between the intermediate water and the measurement water is kept constant.

9. The apparatus for determining total organic carbon according to claim 1, wherein the intermediate water part has a shielding membrane provided so as to be in contact with at least one of the gas-permeable membranes so that the gas-permeable membrane is partially covered with the shielding membrane to regulate the amount of a gas permeating the gas-permeable membrane.

10. The apparatus for determining total organic carbon according to claim 1, wherein the organic-substance oxidation part has a channel through which sample water flows and a UV light incident portion for irradiating the sample water flowing through the channel with UV light.

11. The apparatus for determining total organic carbon according to claim 10, wherein the channel of the organic-substance oxidation part, through which sample water flows, meanders in the UV light incident portion to increase a channel length.

12. The apparatus for determining total organic carbon according to claim 1, wherein part of the sample water channel of the carbon dioxide separation part being in contact with the gas-permeable membrane meanders to increase a channel length.

13. The apparatus for determining total organic carbon according to claim 1, wherein part of the measurement water channel of the carbon dioxide separation part being in contact with the gas-permeable membrane meanders to increase a channel length.

14. The apparatus for determining total organic carbon according to claim 2, wherein part of the intermediate water part of the carbon dioxide separation part being in contact with the gas-permeable membrane meanders to increase a channel length.

15. The apparatus for determining total organic carbon according to claim 1, wherein the intermediate water is a buffer solution having a pH in a neutral region.

16. The apparatus for determining total organic carbon according to claim 1,
   wherein the carbon dioxide separation part is formed by vertically stacking the sample water channel, the intermediate water part, and the measurement water channel with the intermediate water part being interposed between the sample water channel and the measurement water channel to integrate them together,
   wherein the organic-substance oxidation part and the carbon dioxide separation part are vertically stacked to integrate them together, and
   wherein the conductivity measurement part and the carbon dioxide separation part are vertically stacked to integrate them together.

* * * * *